United States Patent [19] [11] 4,035,496
Giordano et al. [45] July 12, 1977

[54] METHODS OF COMBATTING NEMATODES USING CERTAIN DERIVATIVES OF 1,3,5-OXATHIAZINE

[75] Inventors: Claudio Giordano; Mario Ferraris, both of Novara; Elena Barsuglia, S. Donato Milanese (Milan), all of Italy

[73] Assignee: Montedison Fibre S.p.A., Milan, Italy

[21] Appl. No.: 597,094

[22] Filed: July 18, 1975

[30] Foreign Application Priority Data

July 19, 1974 Italy .................................. 25367/74

[51] Int. Cl.$^2$ .......................................... A01N 9/12
[52] U.S. Cl. ................................................ 424/246
[58] Field of Search ................. 424/246; 260/243 R

[56] References Cited

U.S. PATENT DOCUMENTS 3,299,137  1/1967  Payne et al. ......................... 260/566
3,689,485  9/1972  Cuauss et al. .................. 260/243 R

FOREIGN PATENT DOCUMENTS 22,039          Italy

Primary Examiner—Leonard Schenkman

[57] ABSTRACT

Compositions comprising 1,3,5-oxathiazine derivatives and which are highly effective against nematodes but exhibit low toxicity for warm-blooded animals are disclosed.

6 Claims, No Drawings

METHODS OF COMBATTING NEMATODES USING CERTAIN DERIVATIVES OF 1,3,5-OXATHIAZINE

THE PRIOR ART

As is known, nematodes are small worms which infest the soil and by establishing themselves in the roots of plants cause the formation of galls.

Various chemicals have been proposed in the art for combatting nematodes. For instance U.S. Pat. No. 3,217,037 discloses a class of carbamides which are active against nematodes and amongst which the carbamide of formula

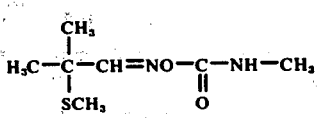

is the most active.

Also, it is known that 1,2-dibromo-3-chloro-propane, marketed as "Fumagone" and "Nemagon" for use as fumigant exhibit nematodocidal action. Other known nematodocides are esters of thiophosphoric acid, such as "Nemafos," which is the O,O-diethyl ester of O-2-pyrazinyl-thiophosphoric acid.

However, those known nematodocides have the disadvantage that they are not well-tolerated by all cultivations, and/or their activity-span is short. In addition, they are all rather highly toxic to warm-blooded animals.

Italian Pat. Appl. 22039 A/73 (Montedison) discloses derivatives of 1,3,5-oxathiazine of the general formula

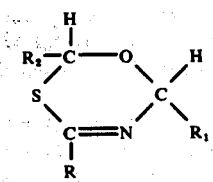

in which R represents an alkyl radical containing from 1 to 10 carbon atoms, an aryl radical containing from 6 to 12 carbon atoms, or an alkylaryl radical; $R_1$ and $R_2$, which can be the same or different, represent hydrogen atoms and/or alkyl radicals containing from 1 to 10 carbon atoms.

THE PRESENT INVENTION

An object of this invention is to provide new nematodocidal compositions which, among other advantages, exhibit low toxicity for warm-blooded animals and the active constituents of which are derivatives of 1,3,5-oxathiazines of the general formula

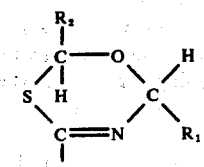

in which R represents an unsubstituted or substituted aryl radical and $R_1$ and $R_2$, which can be the same or different, represent hydrogen atoms or methyl groups.

More particularly, when R is a substituted phenyl radical, the most active nematodocides are those in which the phenyl radical is substituted in the 4-position by halogen or a alkyl radical, or in the 3,4 positions when two substituents, halogen and/or lower alkyl groups are present.

The toxicity in rats of the oxathiazines of the invention is from 300 to over 1,000 mg/kg. The quantity thereof which is applied to the soil is at least 1 ppm.

The application to the soil can be by scattering the active oxathiazines in the form of solutions or suspensions which may also contain emulsifiers, surfactants, and/or pesticides, and/or herbicides, and/or fertilizers. The active oxathiazines may also be scattered on the soil in the solid state, as such, or supported on, or mixed with, other substances as may be desired.

Oxathiazines which have given particularly satisfactory results include:

4-phenyl-6-H-1,3,5-oxathiazine (our mark DIRI 2434),
4-phenyl-2-methyl-6-H-1,3,5-oxathiazine (mark DIRI 2538),
4-(p. tolyl)-6-H-1,3,5-oxathiazine (mark DIRI 2656),
4-(4-chlorophenyl)-6H-1,3,5-oxathiazine (mark DIRI 2635),
4-(4-methoxyphenyl)-6H-1,3,5-oxathiazine (mark DIRI 2657).

The oxathiazines of this invention can be prepared substantially by the method described in the above-mentioned Italian Pat. Appl. No. 22039 A/73 that is by reacting substituted or unsubstituted thiobenzamide with acetaldehyde or formaldehyde in the presence of a non-oxidizing strong acid or of a Lewis acid, at a temperature of from −20° C to +100° C.

The following examples are given to illustrate the invention and are not intended to be limiting.

EXAMPLE 1

Preparation of 4(4-chlorophenyl)-6H-1,3,5-oxathiazines

To a solution of 10.175 g (0.1 mole) of N-hydroxymethyl-p-chlorothiobenzamide and 3 g (equal to 0.1 mole of $CH_2O$) of para-formaldehyde in 100 g of acetic acid, were admixed dropwise a solution consisting of 235 g (0.24 moles) of 100% sulphuric acid in 50 g of acetic acid, while maintaining the temperature at about 15° C. After 50 hours stirring at 15° C, the raw reaction product was poured into ice, alkalized with a 40% NaOH solution at a temperature maintained at about 5° C, and then extracted with ethyl ether.

The etheric extract was then washed with $HCl_2N$ at about 5° C and the aqueous acid solution was alkalized at the same temperature with a 40% solution of NaOH and extracted with ethyl ether. That etheric extract, evaporated to dryness, leaves as residue a solid product with a melting point (m.p.) of 51°–52° C, recognized on the basis of an elementary analysis, from the IR spectrum by the NMR (nuclear magnetic resonance) test and through mass-spectrophotometry as a 4-(4-chlorophenyl)-6H-1,3,5-oxathiazine of the formula:

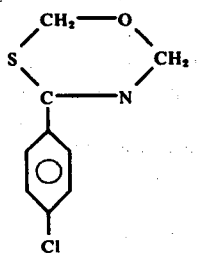

an activity scale going from 0 to 5, where O indicates that there had been no reduction of pest attack, that is, the plants cannot be distinguished from the witness plant, while 5 indicates that there had been no formation of galls (total activity).

The temperature was maintained at 23° C ± 1° C, the relative humidity was maintained at 60 ± 5%. The illumination was achieved with fluorescent tubes of 2500 lux. The photoperiod was 17 hours. The results are recorded in the following TABLE 1.

Product of formula:

$$\begin{array}{c} R_2-CH-O \\ \diagdown \diagup H \\ S \diagdown \diagup C \\ \diagup \diagdown \\ C-N \quad R_1 \\ | \\ R \end{array}$$

| name | R | $R_1$ | $R_2$ | Dose p.p.m. | Activity |
|---|---|---|---|---|---|
| DIRI 2434 | $C_6H_5-$ | H | H | 20 | 5 |
| DIRI 2538 | $C_6H_5-$ | H | $CH_3$ | 100 | 5 |
|  |  |  |  | 20 | 4–5 |
| DIRI 2656 | $pCH_3-C_6H_4-$ | H | H | 20 | 5 |
| DIRI 2635 | $pCl-C_6H_4-$ | H | H | 20 | 5 |
|  |  |  |  | 4 | 4–5 |
| DIRI 2657 | $pCH_3O-C_6H_4-$ | H | H | 20 | 5 |
| WITNESS | — | — | — | — | 0 |

EXAMPLES 2 and 3

Preparation of 4-(p. tolyl)- and 4-(4-methoxyphenyl)-6H-1,3,5-oxathiazines

Following the same procedures as in Example 1, by reacting with paraformaldehyde, respectively N-hydroxymethyl-tolylbenzamide and N-hydroxymethyl-p-methoxybenzamide, there were obtained:

4-(p. tolyl)-6H-1,3,5-oxathiazine with a m.p. = 55°–56° C in a yield of 42%; and
4-(4-methoxyphenyl)-6H-1,3,5-oxathiazine with a m.p. = 66° to 67° C and in a yield of 22.5%.

The elementary analyses, the infrared spectra, the mass spectrophotometries and the NMR confirmed the formulae.

EXAMPLE 4

Test for the screening of the nematodocide activity on *Meloidogyne icognita* Chitwood (Iylenchids, Heteroderidae)

Field soil and sand infested by the addition of chopped up roots of tomato plants on which there had been grown *M incognita* for about 3 months, were mixed together in a volumetric ratio of 1:1. By means of a mechanical mixer, 100 cc of a hydroacetonic solution (20% acetone, vol/vol) of the oxathiazine to be tested was uniformly spread out in 1 kg of soil. This soil was then distributed in pots of plastic material (for control purposes, one pot was filled with soil having the same characteristics and likewise infested, but without nematodocide) with a holding capacity of about 800 cc.

After 5 days, five small tomato plants about 15 cm high were transplanted in each of the pots.

14 days after transplantation, the roots of the tomato plants, extracted from the soil, were examined in order to ascertain the degree of infestation by means of counting the number of galls that had formed on them. The nematodocide action was expressed according to

EXAMPLE 5

Determination of the acute toxicity of $LD_{50}$ by oral administration to rats of a group of products with a nematodocide action according to the invention

A. METHODOLOGY:

Test animal: albino rat, Wistar strain 50% males, 50% females, weighing 100 grams each; 10 animals per each dose.

After a certain stalling period, the rats were kept without food from 6 hours before to 2 hours after the treatment, and subsequently they were kept under observation for 10 days, during which these animals were fed with balanced (calibrated) feed in pellets and with water ad libitum.

The treatment was carried out by introducing into the stomach pre-established quantities of the product under examination by means of a gastrical probe connected with a precision syringe.

On the basis of the percent mortality rate obtained at various doses after 10 days, the $LD_{50}$ was calculated and the gradient of the straight line of regression was established with the fiduciary limits according to the Lichtfield and Wilcoxon statistical method.

B. RESULTS:

DIRI 2434-$LD_{50}$ mg/kg 650; lower and upper fiduciary limits at an error-probability level of 5%, 575–734. The test was carried out on 40 rats, 50% males and 50% females.

DIRI 2538-$LD_{50}$ mg/kg 655, lower and upper fiduciary limits at an error-probability level of 5%; 503–800. The test was carried out on 40 rats, 50% males and 50% females.

DIRI 2635-$LD_{50}$ mg/kg more than 500. The test was carried out on 20 rats, 50% males and 50% females.

DIRI 2656-$LD_{50}$ mg/kg greater than 1000. The test was carried out on 20 rats, 50% males and 50% females.

DIRI 2657-$LD_{50}$ mg/kg about 900. The test was carried out on 40 rats, 50% males and 50% females.

What is claimed is:

1. A method of combatting nematodes infesting soil which consists of applying, to the soil to be treated, a composition the essential nematodocidal constituent of which is a nematodocidally effective amount of at least one 1,3,5-oxathiazine of the general formula:

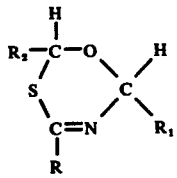

(I)

in which R represents phenyl, phenyl substituted at position 4 by halogen, lower alkyl or methoxy, or phenyl substituted at positions 3-4 by halogen or lower alkyl and $R_1$ and $R_2$, which may be the same or different, represent hydrogen or methyl, which essential constituent has an $LD_{50}$ in the rat greater than 300 mg/kg.

2. The method according to claim 1, in which the essential nematodocidal constituent is 4-phenyl-6H-1,3,5-oxathiazine.

3. The method according to claim 1, in which the essential nematodocidal constituent is 4-phenyl-2-methyl-6H-1,3,5-oxathiazine.

4. The method according to claim 1, in which the essential nematodocidal constituent is 4(p. tolyl)-6H-1,3,5-oxathiazine.

5. The method according to claim 1, in which the essential nematodocidal constituent is 4-(p. chlorophenyl)-6H-1,3,5-oxathiazine.

6. The method according to claim 1, in which the essential nematodocidal constituent is 4-(p. methoxyphenyl)-6H-1,3,5-oxathiazine.

* * * * *

UNITED STATES PATENT OFFICE
CERTIFICATE OF CORRECTION

Patent No. 4,035,496       Dated July 12, 1977

Inventor(s) Claudio GIORDANO et al

It is certified that error appears in the above-identified patent and that said Letters Patent are hereby corrected as shown below:

[73] The assignee should be

Montedison S.p.A., Milan, Italy ( not Montedison Fibre S.p.A., Milan, Italy )

Col. 3, Example 4, line 2, "Iylenchids" should be

- - - Iylenchida - - -.

Col. 4, after line 10, insert

- - - T A B L E 1 - - - above the tabulations given.

Signed and Sealed this

Seventh Day of March 1978

[SEAL]

Attest:

RUTH C. MASON       LUTRELLE F. PARKER
*Attesting Officer*      *Acting Commissioner of Patents and Trademarks*